United States Patent
Yamada et al.

(10) Patent No.: US 8,173,701 B2
(45) Date of Patent: May 8, 2012

(54) PESTICIDAL COMPOSITION AND METHOD FOR CONTROLLING HARMFUL INSECTS

(75) Inventors: Masahiro Yamada, Toyonaka (JP); Yoshito Tanaka, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 143 days.

(21) Appl. No.: 12/593,840

(22) PCT Filed: Mar. 27, 2008

(86) PCT No.: PCT/JP2008/056641
§ 371 (c)(1),
(2), (4) Date: Sep. 29, 2009

(87) PCT Pub. No.: WO2008/123574
PCT Pub. Date: Oct. 16, 2008

(65) Prior Publication Data
US 2010/0113594 A1    May 6, 2010

(30) Foreign Application Priority Data

Mar. 30, 2007    (JP) .................................. 2007-091202

(51) Int. Cl.
*A01N 37/00* (2006.01)
*A61K 31/21* (2006.01)
*A61K 31/26* (2006.01)

(52) U.S. Cl. .......................... 514/506; 514/514; 514/519

(58) Field of Classification Search .................. None
See application file for complete search history.

(56) References Cited

U.S. PATENT DOCUMENTS 5,190,745 A * 3/1993 Dohara et al. .................. 424/45
6,908,945 B2 * 6/2005 Mori ............................. 514/521

FOREIGN PATENT DOCUMENTS

| FR | 2 738 718 A1 | 3/1997 |
| GB | 2 243 297 A | 10/1991 |
| GB | 2243297 | * 10/1991 |
| JP | 2001-328914 A | 11/2001 |
| JP | 2004-2363 A | 1/2004 |
| JP | 2006-273743 A | 10/2006 |
| JP | 2006273743 | * 10/2006 |
| WO | WO-2006/107905 A1 | 10/2006 |
| WO | WO 2008/123571 A2 | 10/2008 |

OTHER PUBLICATIONS

Iwasaki et. al. "Insecticidal mats containing pyrethroid and ester for control of mosquito" XP002534773 retrived from STN Database accession No. 2001:855723, Tokyo, Japan.

Matsumoto et. al. "Insecticide solutions for heat vaporization" XP002534774 retrieved from STN Database accession No. 2006-1059994, Tokyo, Japan.

English translation of Egyptian Office Action issued on Dec. 19, 2010 in corresponding Egyptian Patent Application No. 1352/2009.

* cited by examiner

*Primary Examiner* — Alton Pryor

(74) *Attorney, Agent, or Firm* — Birch, Stewart, Kolasch & Birch, LLP

(57) ABSTRACT

A pesticidal composition containing: 4-methoxymethyl-2,3,5,6-tetrafluorobenzyl 3-(2-cyano-1-propenyl)-2,2-dimethyl-cyclopropanecarboxylate, a saturated hydrocarbon having an initial boiling point of 150 C or higher and a 95%-distillation temperature of 300 C or lower, and at least one alkyl carboxylate ester selected from the group consisting of the following esters (i) to (iii): (i) alkyl alkylcarboxylate esters having 12 to 20 carbon atoms, (ii) dialkyl dicarboxylate esters having 12 to 20 carbon atoms, and (iii) trialkyl acetylcitrate esters having 12 to 20 carbon atoms; has an excellent pesticidal activity.

13 Claims, No Drawings

PESTICIDAL COMPOSITION AND METHOD FOR CONTROLLING HARMFUL INSECTS

FIELD OF THE INVENTION

The present invention relates to a pesticidal composition and a method for controlling harmful insects.

DESCRIPTION OF THE RELATED ART

JP2004-2363A describes that 4-methoxymethyl-2,3,5,6-tetrafluorobenzyl 3-(2-cyano-1-propenyl)-2,2-dimethylcyclopropanecarboxylate has a pesticidal activity, while Formulation Examples and Test Examples in JP2004-2363A describe compositions containing the compound, dichloromethane and kerosene.

SUMMARY OF THE INVENTION

An object of the present invention is to provide a pesticidal composition having an excellent pesticidal activity and a method for controlling harmful insects.

After intensive studies to find a pesticidal composition having an excellent pesticidal activity and a method for controlling harmful insects, the inventors have found that a pesticidal composition containing: 4-methoxymethyl-2,3,5,6-tetrafluorobenzyl 3-(2-cyano-1-propenyl)-2,2-dimethylcyclopropanecarboxylate, a saturated hydrocarbon having an initial boiling point of 150° C. or higher and a 95%-distillation temperature of 300° C. or lower, and at least one alkyl carboxylate ester selected from the group consisting of:

(i) alkyl alkylcarboxylate esters having 12 to 20 carbon atoms;

(ii) dialkyl dicarboxylate esters having 12 to 20 carbon atoms; and (iii) trialkyl acetylcitrate esters having 12 to 20 carbon atoms, has an excellent pesticidal activity, and achieved the present invention.

The present invention provides:

1. A pesticidal composition comprising:
4-methoxymethyl-2,3,5,6-tetrafluorobenzyl 3-(2-cyano-1-propenyl)-2,2-dimethylcyclopropanecarboxylate,
a saturated hydrocarbon having an initial boiling point of 150° C. or higher and a 95%-distillation temperature of 300° C. or lower, and
at least one alkyl carboxylate ester selected from the group consisting of:
(i) alkyl alkylcarboxylate esters having 12 to 20 carbon atoms;
(ii) dialkyl dicarboxylate esters having 12 to 20 carbon atoms; and
(iii) trialkyl acetylcitrate esters having 12 to 20 carbon atoms;

2. The pesticidal composition described in 1, wherein the composition comprises the saturated hydrocarbon in an amount of 0.5 to 10 parts by weight per part by weight of the alkyl carboxylate ester;

3. The pesticidal composition described in 1 or 2, wherein the composition comprises 4-methoxymethyl-2,3,5,6-tetrafluorobenzyl 3-(2-cyano-1-propenyl)-2,2-dimethylcyclopropanecarboxylate in an amount of 0.00001 to 0.1 part by weight per part by weight of the alkyl carboxylate ester;

4. The pesticidal composition described in any one of 1 to 3, wherein the composition content of 4-methoxymethyl-2,3,5,6-tetrafluorobenzyl 3-(2-cyano-1-propenyl)-2,2-dimethylcyclopropanecarboxylate in an amount of 0.0001 to 0.5% by weight;

5. The pesticidal composition described in any one of 1 to 4, wherein the alkyl carboxylate ester is at least one member selected from the group consisting of diisopropyl adipate, isopropyl myristate and tributyl acetylcitrate;

6. The pesticidal composition described in any one of 1 to 3, wherein the composition is for controlling insects Blattaria;

7. A method for controlling harmful insects, which comprises applying an effective amount of a pesticidal composition comprising: 4-methoxymethyl-2,3,5,6-tetrafluorobenzyl 3-(2-cyano-1-propenyl)-2,2-dimethylcyclopropanecarboxylate, a saturated hydrocarbon having an initial boiling point of 150° C. or higher and a 95%-distillation temperature of 300° C. or lower, and at least one alkyl carboxylate ester selected from the group consisting of:
(i) alkyl alkylcarboxylate esters having 12 to 20 carbon atoms,
(ii) dialkyl dicarboxylate esters having 12 to 20 carbon atoms, and
(iii) trialkyl acetylcitrate esters having 12 to 20 carbon atoms,
on harmful insect or a locus where the insect inhabits;

8. The method described in 7, wherein the composition comprises the saturated hydrocarbon in an amount of 0.5 to 10 parts by weight per part by weight of the alkyl carboxylate ester;

9. The method described in 7 or 8, wherein the composition comprises 4-methoxymethyl-2,3,5,6-tetrafluorobenzyl 3-(2-cyano-1-propenyl)-2,2-dimethylcyclopropanecarboxylate in an amount of 0.00001 to 0.1 part by weight per part by weight of the alkyl carboxylate ester;

10. The method described in any one of 7 to 9, wherein the composition comprises 4-methoxymethyl-2,3,5,6-tetrafluorobenzyl 3-(2-cyano-1-propenyl)-2,2-dimethylcyclopropanecarboxylate in an amount of 0.0001 to 0.5% by weight;

11. The method described in any one of 7 to 10, wherein the alkyl carboxylate ester is at least one member selected from the group consisting of diisopropyl adipate, isopropyl myristate and tributyl acetylcitrate;

12. The method described in any one of 7 to 11, wherein the composition is for controlling insects Blattaria; and 13. A pest control agent comprising the pesticidal composition described in any one of 1 to 6.

The pesticidal composition according to the present invention has an excellent pesticidal activity. It is also possible to control harmful insects by using the method for controlling harmful insects according to the present invention.

DETAILED DESCRIPTION OF THE INVENTION

A pesticidal composition according to the present invention (hereinafter, referred to as the inventive composition) contains 4-methoxymethyl-2,3,5,6-tetrafluorobenzyl 3-(2-cyano-1-propenyl)-2,2-dimethylcyclopropanecarboxylate, a saturated hydrocarbon and an alkyl carboxylate ester.

4-Methoxymethyl-2,3,5,6-tetrafluorobenzyl 3-(2-cyano-1-propenyl)-2,2-dimethylcyclopropanecarboxylate (hereinafter, referred to as the Ester compound) for use in the invention is, for example, a compound described in U.S. Pat. No. 6,908,945 and can be prepared according to the method described therein.

The Ester compound has isomers, attributable to the two asymmetric carbon atoms present in the cyclopropane ring and also isomers derived from the double bond, but each isomer and a mixture of the isomers at any rate are also included in the Ester compound.

In the present invention, as the saturated hydrocarbons, used are various saturated hydrocarbon solvents having an initial boiling point of 150° C. or higher and a 95%-distillation temperature of 300° C. or lower (hereinafter, referred to as the Saturated Hydrocarbon) substantially containing at least one solvent selected from various saturated hydrocarbons (straight-chain saturated hydrocarbons, branched-chain saturated hydrocarbons, and alicyclic saturated hydrocarbons), and those having an initial boiling point of 150° C. or higher and a dry point of 300° C. or lower may also be used. Examples of the Saturated Hydrocarbon solvents include Isopar G (manufactured by Exxon Mobil Corp., initial boiling point: 160° C., dry point: 176° C.), Isopar L (manufactured by Exxon Mobil Corp., initial boiling point: 189° C., dry point: 207° C.), Isopar H (manufactured by Exxon Mobil Corp., initial boiling point: 178° C., dry point: 188° C.), Isopar M (manufactured by Exxon Mobil Corp., initial boiling point: 223° C., dry point: 254° C.), Norpar 13 (manufactured by Exxon Mobil Corp., initial boiling point: 222° C., dry point: 242° C.), Norpar 15 (manufactured by Exxon Mobil Corp., initial boiling point: 249° C., dry point: 274° C.), Exxsol D40 (manufactured by Exxon Mobil Corp., initial boiling point: 164° C., dry point: 192° C.), Exxsol D60 (manufactured by Exxon Mobil Corp., initial boiling point: 187° C., dry point: 209° C.), Exxsol D80 (manufactured by Exxon Mobil Corp., initial boiling point: 208° C., dry point: 243° C.), Neochiozol (manufactured by Chuokasei Co., Ltd., initial boiling point: 225° C., dry point: 247° C.), IP solvent 2028 (manufactured by Idemitsu Kosan Co., Ltd., initial boiling point: 213° C., 95%-distillation temperature: 250° C.) and kerosene.

The alkyl carboxylate in the present invention is, for example, at least one alkyl carboxylate ester (hereinafter, referred to as the Ester) selected from the group consisting of:

(i) alkyl alkylcarboxylate esters having 12 to 20 carbon atoms;

(ii) dialkyl dicarboxylate esters having 12 to 20 carbon atoms; and (iii) trialkyl acetylcitrate esters having 12 to 20 carbon atoms.

Specifically, examples of (i) the alkyl alkylcarboxylate esters having 12 to 20 carbon atoms include isopropyl palmitate, isopropyl myristate and hexyl laurate.

Examples of (ii) the dialkyl dicarboxylate esters having 12 to 20 carbon atoms include diisopropyl adipate, dihexyl adipate, diethyl sebacate and dibutyl sebacate.

Examples of (iii) the trialkyl acetylcitrate esters having 12 to 20 carbon atoms include triethyl acetylcitrate and tributyl acetylcitrate.

As for the amounts of the Saturated Hydrocarbon and the Ester according to the inventive composition, the Saturated Hydrocarbon is contained usually in an amount of 0.5 to 10 parts by weight per part by weight of the Ester, and the Saturated Hydrocarbon and the Ester in the inventive composition are contained in a total amount usually of 90 to 99.999% by weight, preferably 95 to 99.999% by weight.

As for the amounts of the Ester compound and the Ester in the inventive composition, the Ester compound is contained usually in an amount of 0.00001 to 0.1 part by weight per part by weight of the Ester, and the Ester compound is contained in an amount usually of 0.00001 to 0.5% by weight, preferably 0.001 to 0.5% by weight in the inventive composition.

The inventive composition may contain, as needed, one or more of additional additives such as other insecticidally active ingredients, acaricidally active ingredients, repellently active ingredients, synergists, and flavoring agents.

Examples of the insecticidally active ingredients and acaricidally active ingredients include organic phosphorus compounds such as Fenitrothion, Fenthion, Diazinon, Chlorpyrifos, Acephate, Methidathion, Disulfoton, DDVP, Sulprofos, Cyanophos, Dioxabenzophos, Demethoate, Phenthoate, Malathion, Trichlorfon, Azinphosmethyl, Monocrotophos, Ethion, Dichlorvos, Profenofos, Sulprofos, Phenthoate, Isoxathion, Tetrachlorvinphos, Terbufos, Phorate, Chlorethoxyfos, Fosthiazate, Ethoprophos and Cadusafos; carbamate compounds such as BPMC, Benfuracarb, Propoxur, Carbosulfan, Carbaryl, Methomyl, Ethiofencarb, Aldicarb, Oxamyl, Fenothiocarb, Thiodicarb, Alanycarb, Methiocarb and Cartap; pyrethroid compounds such as Etofenprox, Fenvalerate, Esfenvalerate, Fenpropathrin, Cycloprothrin, Fluvalinate, tau-Fluvalinate, Bifenthrin, Halfenprox, Tralomethrin, Silafluofen, d-Resmethrin, Acrinathrin, Tefluthrin, Transfluthrin, Tetramethrin, Allethrin, d-Furamethrin, Prallethrin, Empenthrin, Flucythrinate, Flumethrin, and 5-(2-propynyl)furfuryl 2,2,3,3-tetramethylcyclopropanecarboxylate; Acetamiprid, Nitenpyram, Thiacloprid, Thiamethoxam, Dinotefuran, Clothianidin, Imidacloprid, etc; chlorinated hydrocarbon compounds such as Endosulfan, γ-BHC, and 1,1-bis(chlorophenyl)-2,2,2-trichloroethanol; benzoylphenyl urea compounds such as Chlorfluazuron, Teflubenzuron, Fulfenoxlon, Lufenuron, Hexaflumuron, Diflubenzuron, Triflumuron, Fluazuron, Novaluron, Triazuron and Bistrifluoron; phenylpyrazole compounds such as Acetoprole, Pyriprole, Pyrafluprole and Ethiprole; benzoylhydrazine compounds such as Tebufenozide, Chromafenozide, Methoxyfenozide and Halofenozide; Metoxadiazone; Bromopropylate; Tetradifon; Chinomethionate; Pyridaben; Fenpyroximate; Diafenthiuron; Tebufenpyrad; Pymetrozine; Fronicamide; Triazamate; Buprofezin; Chlorfenapyr; Indoxacarb; Pyridalyl; Cyromazine; Fluacrypyrim; Etoxazole; Fenazaquin; Acequinocyl; Hexythiazox; Clofentezine; Fenbutatin oxide; Dicofol; Propargite; Amitraz; Bensultap; Thiocyclam; Spirodiclofen; Spiromesifen; Amidoflumet; Metaflumizone; Flubendiamide; Chlorantraniliprole; pyrifluquinazon; Polynactin complexes [tetranactin, dinactin and trinactin]; Pyrimidifen; Milbemectin; Abamectin; Spinosad; Emamectin benzoate; Ivermectin; and Azadirachtin.

Examples of the repellently active ingredients include 3,4-caranediol, N,N-diethyl-m-toluamide, 1-methylpropyl 2-(2-hydroxyethyl)-1-piperidinecarboxylate, limonene, linalool, citronellal, menthol, menthone, hinokitiol, geraniol, eucalyptol, p-menthane-3,8-diol, and plant essential oils such as hyssop oil.

Examples of the synergists include bis-(2,3,3,3-tetrachloropropyl)ether [S-421], N-(2-ethylhexyl)bicyclo[2.2.1]hept-5-ene-2,3-dicarboxyimide [product name: MGK-264], α-[2-(2-butoxyethoxy)ethoxy]-4,5-methylenedioxy-2-propyltoluene[piperonyl butoxide], IBTA (Isobornyl thiocyanatoacetate) and N-(2-ethylhexyl)-1-isopropyl-4-methylbicyclo[2,2,2]-octa-5-ene-2,3-dicarboxylmide (product name: Synepirin 500).

Examples of the harmful insects that can be controlled with the inventive composition include arthropods such as insects and mites, and typical examples include the followings:

Lepidoptera: Pyralidae such as *Chilo suppressalis, Cnaphalocrocis medinalis*, and *Plodia interpunctella*; Noctuidae such as *Spodoptera litura, Pseudaletia separata*, and *Mamestra brassicae*; Pieridae such as *Pieris rapae crucivora*; ortricidae such as *Adoxophyes orana*; Carposimidae; Lyonetiidae; Lymantriidae; Antographa; *Agrotis* spp. such as *Agrotis segetum* and *Agrotis ipsilon; Helicoverpa* spp., *Heliothis* spp., *Plutella xylostella, Parnara guttata guttata, Tinea pellionella, Tineola bisselliella*, etc.

Diptera: *Culex* such as *Culex pipiens pallens, Culex tritaeniorhynchus* and *Culex quinquefasciatus*; *Aedes* such as *Aedes aegypti* and *Aedes albopictus*; Anophelinae such as *Anopheles sinensis* and *Anopheles gambiae*; Chironomidae; Muscidae such as *Musca domestica, Muscina stabulans*, and *Fannia canicularis*; Calliphoridae; Sarcophagidae; Anthomyiidae such as *Delia platura* and *Delia antiqua*; Tephritidae; Drosophilidae; Psychodidae; Phoridae; Tabanidae; Simuliidae; Culicoides; Ceratopogonidae; etc.

Blattaria: *Blattella germanica, Periplaneta fuliginosa, Periplaneta americana, Periplaneta brunnea, Lobopterella dimidiatipes*, etc.

Hymenoptera: Formicidae, Vespidae, Bethylidae; Tenthredinidae such as *Athalia rosae ruficornis*, etc.

Siphonaptera: *Ctenocephalides canis, Ctenocephalides felis felis, Pulex irritans*, etc.

Anoplura: *Pediculus humanus, Pthirus pubis, Pediculus capitis, Pediculus humanus*, etc.

Isoptera (termites): *Reticulitermes speratus speratus, Coptotermes formosanus*, etc.

Hemiptera: Delphacidae such as *Laodelphax stratella, Nilaparvata lugens*, and *Sogatella furcifera*; Deltocephalidae such as *Nephotettix cincticeps* and *Nephotettix virescens*; Aphididae; Pentatomidae; Aleyrodidae; Coccoidae; Tingidae; Psyllidae; Cimicidae; etc.

Coleoptera: *Attagenus japonicus, Anthrenus verbasci*; corn rootworms such as Western corn rootworm, and Southern corn rootworm; Scarabaeidae such as *Anomala cuprea* and *Anomala rufocuprea*; Curculionidae such as *Sitophilus zeamais, Lissorhoptrus oryzophilus, Anthonomus grandis grandis*, and *Callosobruchus chinensis*; Tenebrionidae such as *Tenebrio molitor* and *Tribolium castaneum*; Chrysomelidae such as *Oulema oryzae, Phyllotreta striolata*, and *Aulacophora femoralis*; Anobiidae, *Epilachna* spp. such as *Epilachna vigintioctopunctata*; Lyctidae; Bostrychidae; Cerambycidae; *Paederus fuscipes*; etc.

Thysanoptera (thrips): *Thrips palmi, Frankliniella occidentalis, Thrips hawaiiensis*, etc.

Orthoptera: Gryllotalpidae, Acrididae, etc.

Acarines: Pyroglyphidae such as *Dermatophagoides farinae* and *Dermatophagoides pteronyssinus*; Acaridae such as *Tyrophagus putrescentiae* and *Aleuroglyphus ovatus*; Glycyphagidae such as Glycyphagidae *privatus*, Glycyphagidae *domesticus*, and *Glycyphagus destructor*; Cheyletidae such as *Cheyletus malaccensis* and *Cheyletus fortis*; Tarsonemidae; Chortoglyphidae; Haplochthoniidae; Tetranychidae such as *Tetranychus urticae, Tetranychus Kanzawai, Panonychus citri*, and *Panonychus ulmi*; Ixodidae such as *Haemaphysalis longicornis*; etc.

The inventive composition is prepared, for example, by mixing and dissolving the Ester compound, the Saturated Hydrocarbon and the Ester, and as needed the other insecticidally active ingredient, acaricidally active ingredient, repellently active ingredient, synergist, flavoring agent and others, at room temperature or under heat.

When the inventive composition is used for controlling harmful insects, the inventive composition may be applied as it is or in the form of a pest controlling agent formulation containing the inventive composition.

The formulations include, for example, oil, emulsion, water-dispersible powder, flowable agent (aqueous suspension, aqueous emulsion, etc.), powder, granule, aerosol, heated vaporization agent (insecticide coil, insect electrocuting mat, heated insecticide-vaporizing agent with liquid-absorbing shaft, etc.), heated fumigant (self-combustion fumigant, chemical-reaction fumigant, porous-ceramic-plate fumigant, etc.), unheated vaporization agent (resin vaporization agent, impregnated paper vaporization agent, etc.), spraying agent (fogging, etc.), ULV agent, and poisonous bait.

These formulations are produced, for example, by the following methods.

(1) a method comprising mixing the inventive composition with a solid carrier, liquid carrier, gaseous carrier, bait, or the like, and additionally other auxiliaries for formulation such as surfactant if needed, and processing the resultant mixture;

(2) a method comprising impregnating a base material with the inventive composition; and (3) a method comprising mixing the inventive composition with a base material and molding the resultant mixture.

The inventive composition is usually contained in a total amount of 0.1 to 95% by weight in these formulations, although the content varies depending on the form of the formulation.

Examples of the solid carriers used for formulation include clays (kaolin clay, diatomaceous earth, synthetic hydrated silicon oxide, bentonite, Fubasami clay, acid clay, etc.), talcs, ceramics, other inorganic minerals (sericite, quartz, sulfur, activated carbon, calcium carbonate, Hydration silica, montmorillonite, etc.), and chemical fertilizers (ammonium sulfate, ammonium phosphate, ammonium nitrate, urea, ammonium chloride, etc.). Examples of the liquid carriers include water, alcohols (methanol, ethanol, etc.), ketones (acetone, methylethylketone, etc.), aromatic hydrocarbons (benzene, toluene, xylene, ethylbenzene, methylnaphthalene, phenyl xylyl ethane, etc.), nitriles (acetonitrile, isobutylonitrile, etc.), acid amides (N,N-dimethylformamide, N,N-dimethylacetamide, etc.), and dimethylsulfoxide, vegetable oils (soy bean oil, cottonseed oil, etc.). Examples of the gaseous carriers include CFC gases, butane gas, LPG (liquefied petroleum gas), dimethylether, and carbon dioxide gas.

The surfactant includes, for example, alkyl sulfate salts, alkylsulfonates, alkylarylsulfonates, alkyl arylethers and their polyoxyethylene adducts, polyethylene glycol ethers, polyhydric alcohol esters and sugar alcohol derivatives.

Other auxiliaries for formulation include an adhesive agent, a dispersing reagent, a stabilizer, and others, and examples thereof include casein, gelatin, polysaccharides (starch, gum arabic, cellulose derivative, alginic acid, etc.), lignin derivatives, bentonite, synthetic water-soluble polymers (polyvinylalcohol, polyvinylpyrrolidone), polyacrylic acid, BHT (2,6-di-tert-butyl-4-methylphenol), and BHA (mixture of 2-tert-butyl-4-methoxyphenol and 3-tert-butyl-4-methoxyphenol).

The base material of the insecticide coil is, for example, a mixture of a vegetable powder such as wood powder or sake lees powder and a binder such as tabu powder (powdered leaves of the *Machilus thunbergii* tree), starch, or gluten.

The base material for the insect electrocuting mat is, for example, a cotton linter molded into the plate shape, or a molding of a mixed fibril of cotton linter and pulp in the plate shape.

Examples of the base materials for the self-combustion fumigant include combustible heat-generating agents such as nitrate salts, nitrite salts, guanidine salts, potassium chlorate, nitrocellulose, ethylcellulose, and wood powder; thermal decomposition stimulants such as alkali-metal salts, alkali-earth metal salts, dichromate salts, and chromate salts; oxygen-supplying agents such as potassium nitrate; combustion aides such as melamine and wheat starch; fillers such as diatomaceous earth; and binders such as synthetic adhesives.

Examples of the base materials for the chemical-reaction fumigant include heat-generating agents such as alkali metal sulfides, polysulfides, hydrosulfides and calcium oxide; catalysts such as carbonaceous substances, iron carbide, and activated clay; organic foaming agents such as azo dicarbonamide, benzenesulfonyl hydrazide, dinitropentamethylenetetramine, polystyrene, and polyurethane; and fillers such as natural and synthetic fibrils.

Examples of the base materials for the unheated vaporization agent include thermoplastic resins and papers (filter paper, Japanese paper, etc.).

Examples of the base materials for the poisonous bait include feedstuff components such as grain powder, vegetable oil, saccharides, and crystalline cellulose; antioxidants such as dibutylhydroxytoluene and nordihydroguaiaretic acid; preservatives such as dehydroacetic acid; stimulants for prevention of unintended intake by children or pets such as red pepper powder; and insect-attracting flavors such as of cheese, onion, and peanut oil.

The method for controlling harmful insect according to the present invention is practiced by applying the inventive composition or the formulation thereof on the harmful insect or a locus where the insect inhabits.

The method for applying the inventive composition or the formulation thereof includes specifically the following methods, and is selected properly according to the shape, the use site and others of the inventive composition or the formulation thereof.

(1) a method comprising applying the inventive composition or the formulation thereof on the harmful insect or a locus the insect inhabits as it is.
(2) a method comprising diluting the inventive composition or the formulation thereof with a solvent such as water and applying the diluted mixture on the harmful insect or a locus where the insect inhabits.

In this case, the formulation of the inventive composition or the preparation thereof, such as emulsion, water-dispersible powder, flowable agent, or microcapsular formulation, is usually diluted to a total concentration of the Ester compounds at 0.1 to 10,000 ppm.

(3) a method comprising heating the inventive composition or the formulation thereof and thus, vaporizing the active ingredient therein at a locus where the insect inhabits.

In this case, the dosage and the dosage concentration of the Ester compound are determined respectively, properly according to the shape, application period, application site, and application method of the inventive composition or the formulation thereof and also to the kind of the insects, the damage by the insects, and others.

EXAMPLES

Hereinafter, the present invention will be described more in detail with reference to Preparative Examples, Test Examples, and others, but the present invention is not limited to these Examples.

Preparative Examples for the inventive compositions will be described first. In the following, "part" means "part by weight."

Preparative Example 1

0.00156 part of 4-methoxymethyl-2,3,5,6-tetrafluorobenzyl (Z)-1R-trans-3-(2-cyano-1-propenyl)-2,2-dimethylcyclopropanecarboxylate, 10 parts of diisopropyl adipate and the balance of Neochiozol (manufactured by Chuokasei Co., Ltd., initial boiling point: 225° C., dry point: 247° C.) were mixed and agitated at room temperature for 5 minutes, to give 100 parts of a liquid composition (hereinafter, referred to as the inventive composition (1)).

Preparative Example 2

0.00156 part of 4-methoxymethyl-2,3,5,6-tetrafluorobenzyl (Z)-1R-trans-3-(2-cyano-1-propenyl)-2,2-dimethylcyclopropanecarboxylate, 10 parts of isopropyl myristate and the balance of Neochiozol (manufactured by Chuokasei Co., Ltd., initial boiling point: 225° C., dry point: 247° C.) were mixed and agitated at room temperature for 5 minutes, to give 100 parts of a liquid composition (hereinafter, referred to as the inventive composition (2)).

Preparative Example 3

0.00156 part of 4-methoxymethyl-2,3,5,6-tetrafluorobenzyl (Z)-1R-trans-3-(2-cyano-1-propenyl)-2,2-dimethylcyclopropanecarboxylate, 10 parts of tributyl acetylcitrate and the balance of Neochiozol (manufactured by Chuokasei Co., Ltd., initial boiling point: 225° C., dry point: 247° C.) were mixed and agitated at room temperature for 5 minutes, to give 100 parts of a liquid composition (hereinafter, referred to as the inventive composition (3)).

Hereinafter, preparation of a comparative liquid composition is described in the following Reference Preparative Example.

Reference Preparative Example 1

0.00156 part of 4-methoxymethyl-2,3,5,6-tetrafluorobenzyl (Z)-1R-trans-3-(2-cyano-1-propenyl)-2,2-dimethylcyclopropanecarboxylate, 10 parts dichloromethane and the balance of Neochiozol (manufactured by Chuokasei Co., Ltd., initial boiling point: 225° C., dry point: 247° C.) were mixed and agitated at room temperature for 5 minutes, to give 100 parts of a liquid composition (hereinafter, referred to as the comparative composition (1)).

Hereinafter, Test Examples concerning the advantageous effects of the inventive compositions will be described.

Test Example 1

Ten cockroaches Blattella germanica (5 males and 5 females) were placed in a test container with butter applied on the internal wall (diameter 8.75 cm, height 7.5 cm, bottom face: 16 mesh metal gauze). The container was placed on the bottom of a test chamber (bottom face: 46 cm×46 cm, height: 70 cm). 1.5 g of the inventive composition (1) was sprayed with a spray gun from a height of 60 cm above the container top face (spray pressure: 0.4 kg/cm$^2$). 30 minutes after spraying, the container was removed from the test chamber. The cockroaches Blattella germanica were collected from the container, placed in a clean polyethylene cup (bottom face diameter: 8.2 cm), fed with bait and water, and left still at room temperature, while the container was covered with a cap having a ventilation hole. The mortality of the cockroaches after three days was determined (average of duplicate).

The same procedures as above were repeated except that the inventive composition (1) was replaced with either the inventive composition (2), the inventive composition (3) or the comparative composition (1) to determine the mortality (average of duplicate).

The results are summarized in Table 1.

TABLE 1

|  | Mortality (%) |
| --- | --- |
| Inventive composition (1) | 60 |
| Inventive composition (2) | 70 |
| Inventive composition (3) | 55 |
| Comparative composition (1) | 20 |

The invention claimed is:

1. A pesticidal composition comprising:
    4-methoxymethyl-2,3,5,6-tetrafluorobenzyl 3-(2-cyano-1-propenyl)-2,2-dimethylcyclopropanecarboxylate,
    a saturated hydrocarbon having an initial boiling point of 150° C. or higher and a 95%-distillation temperature of 300° C. or lower, and
    at least one alkyl carboxylate ester selected from the group consisting of:
    (i) alkyl alkylcarboxylate esters having 12 to 20 carbon atoms,
    (ii) dialkyl dicarboxylate esters having 12 to 20 carbon atoms, and
    (iii) trialkyl acetyleitrate esters having 12 to 20 carbon atoms.

2. The pesticidal composition according to claim 1, wherein the composition comprises the saturated hydrocarbon in an amount of 0.5 to 10 parts by weight per part by weight of the alkyl carboxylate ester.

3. The pesticidal composition according to claim 1 or 2, wherein the composition comprises 4-methoxymethyl-2,3,5,6-tetrafluorobenzyl 3-(2-cyano-1-propenyl)-2,2-dimethylcyclopropanecarboxylate in an amount of 0.00001 to 0.1 part by weight per part by weight of the alkyl carboxylate ester.

4. The pesticidal composition according to claim 1, wherein the composition comprises 4-methoxymethyl-2,3,5,6-tetrafluorobenzyl 3-(2-cyano-1-propenyl)-2,2-dimethylcyclopropanecarboxylate in an amount of 0.0001 to 0.5% by weight.

5. The pesticidal composition according to claim 1, wherein the alkyl carboxylate ester is at least one member selected from the group consisting of diisopropyl adipate, isopropyl myristate and tributyl acetylcitrate.

6. The pesticidal composition according to claim 1, wherein the composition is effective in controlling insects Blattaria.

7. A method for controlling harmful insect, which comprises applying an effective amount of a pesticidal composition comprising:
    4-methoxymethyl-2,3,5,6-tetrafluorobenzyl 3-(2-cyano-1-propenyl)-2,2-dimethylcyclopropanecarboxylate,
    a saturated hydrocarbon having an initial boiling point of 150° C. or higher and a 95%-distillation temperature of 300° C. or lower, and
    at least one alkyl carboxylate ester selected from the group consisting of:
    (i) alkyl alkylcarboxylate esters having 12 to 20 carbon atoms,
    (ii) dialkyl dicarboxylate esters having 12 to 20 carbon atoms, and
    (iii) trialkyl acetylcitrate esters having 12 to 20 carbon atoms;
    on the harmful insect or a locus where the insect inhabits.

8. The method according to claim 7, wherein the composition comprises the saturated hydrocarbon in an amount of 0.5 to 10 parts by weight per part by weight of the alkyl carboxylate ester.

9. The method according to claim 7 or 8, wherein the composition comprises 4-methoxymethyl-2,3,5,6-tetrafluorobenzyl 3-(2-cyano-1-propenyl)-2,2-dimethylcyclopropanecarboxylate in an amount of 0.00001 to 0.1 part by weight per part by weight of the alkyl carboxylate ester.

10. The method according to claim 7, wherein the composition comprises 4-methoxymethyl-2,3,5,6-tetrafluorobenzyl 3-(2-cyano-1-propenyl)-2,2-dimethylcyclopropanecarboxylate in an amount of 0.0001 to 0.5% by weight.

11. The method according to claim 7, wherein the alkyl carboxylate ester is at least one member selected from the group consisting of diisopropyl adipate, isopropyl myristate and tributyl acetylcitrate.

12. The method according to claim 7, wherein the composition is effective in controlling insects Blattaria.

13. A pest control agent comprising the pesticidal composition according to claim 1.

* * * * *